(12) United States Patent
Thawer et al.

(10) Patent No.: US 11,559,634 B2
(45) Date of Patent: Jan. 24, 2023

(54) TIP DETERMINER FOR AN INJECTION DEVICE

(71) Applicant: ARES TRADING S.A., Aubonne (CH)

(72) Inventors: Alim Thawer, Cambridge (GB);
Matthew J. Hayes, Cambridge (GB);
Quentin Le Masne, Divonne les Bains (FR); Fabien Jeannerot, Versailles (FR)

(73) Assignee: ARES TRADING S.A., Aubonne (CH)

( * ) Notice: Subject to any disclaimer, the term of this patent is extended or adjusted under 35 U.S.C. 154(b) by 592 days.

(21) Appl. No.: 16/610,365

(22) PCT Filed: May 3, 2018

(86) PCT No.: PCT/EP2018/061409
§ 371 (c)(1),
(2) Date: Nov. 1, 2019

(87) PCT Pub. No.: WO2018/202806
PCT Pub. Date: Nov. 8, 2018

(65) Prior Publication Data
US 2020/0054842 A1  Feb. 20, 2020

(30) Foreign Application Priority Data

May 5, 2017 (EP) .................................. 17169782

(51) Int. Cl.
*A61M 5/42* (2006.01)
*A61M 5/32* (2006.01)
*A61M 5/20* (2006.01)

(52) U.S. Cl.
CPC ................ *A61M 5/42* (2013.01); *A61M 5/20* (2013.01); *A61M 5/3245* (2013.01); *A61M 2005/206* (2013.01)

(58) Field of Classification Search
CPC .......... A61M 5/158; A61M 5/32; A61M 5/46; A61M 2205/3306; A61M 2205/583;
(Continued)

(56) References Cited

U.S. PATENT DOCUMENTS 8,311,615 B2 * 11/2012 Zemel ................ A61B 5/15003
600/473
2012/0165625 A1 * 6/2012 Kohler ............... A61B 5/14556
600/316

(Continued)

FOREIGN PATENT DOCUMENTS

CN        103791852 B    2/2017
WO       2014090252 A1   6/2014

OTHER PUBLICATIONS

International Search Report and Written Opinion of the International Searching Authority, dated Aug. 8, 2018, corresponding to counterpart International Application No. PCT/EP2018/061409; 12 pages.

*Primary Examiner* — Nathan R Price
*Assistant Examiner* — Justin L Zamory
(74) *Attorney, Agent, or Firm* — Carter, DeLuca & Farrell LLP; Carmella L. Stephens

(57) ABSTRACT

A system determines the location of a tip of a hypodermic needle by moving a needle along a path, shining light from two sources onto respective portions of the path, and analysing signals received from the respective light sources that have been reflected by the needle.

14 Claims, 11 Drawing Sheets

(58) Field of Classification Search
CPC .................. A61B 5/061; A61B 5/6848; A61B 2090/3941; A61B 2090/373; A61B 17/3403; A61B 2034/2055
See application file for complete search history.

(56) References Cited

U.S. PATENT DOCUMENTS

2012/0271197 A1* 10/2012 Castle .............. A61B 5/150946
 600/583
2016/0089056 A1* 3/2016 Li .......................... A61B 5/063
 600/409

* cited by examiner

TIP DETERMINER FOR AN INJECTION DEVICE

FIELD

This disclosure relates to a system for determining the location of a tip of a needle, and in particular, but without limitation, to an optical detector system for determining the location of a tip of a hypodermic needle within a medical device such as an autoinjector.

BACKGROUND

Treatment for certain medical conditions can require frequent medicament administration. Percutaneous injection, often accomplished using a syringe having a hypodermic needle, is a common method of administering medicaments. Automated handheld injection devices (autoinjectors) allow a user to place a medicament container, such as a syringe, inside the autoinjector and, upon actuation of the autoinjector, inject a predetermined dosage of the medicament into their body. Different types of injection, for example intravenous, intramuscular, and subcutaneous injections require different needle penetration depths.

SUMMARY

Aspects and features of an invention are set out in the appended claims.

BRIEF DESCRIPTION OF THE DRAWINGS

Examples of the present disclosure will now be explained with reference to the accompanying drawings, in which.

Throughout the description and the drawings, like reference numerals refer to like parts.

DETAILED DESCRIPTION

Figure 1:
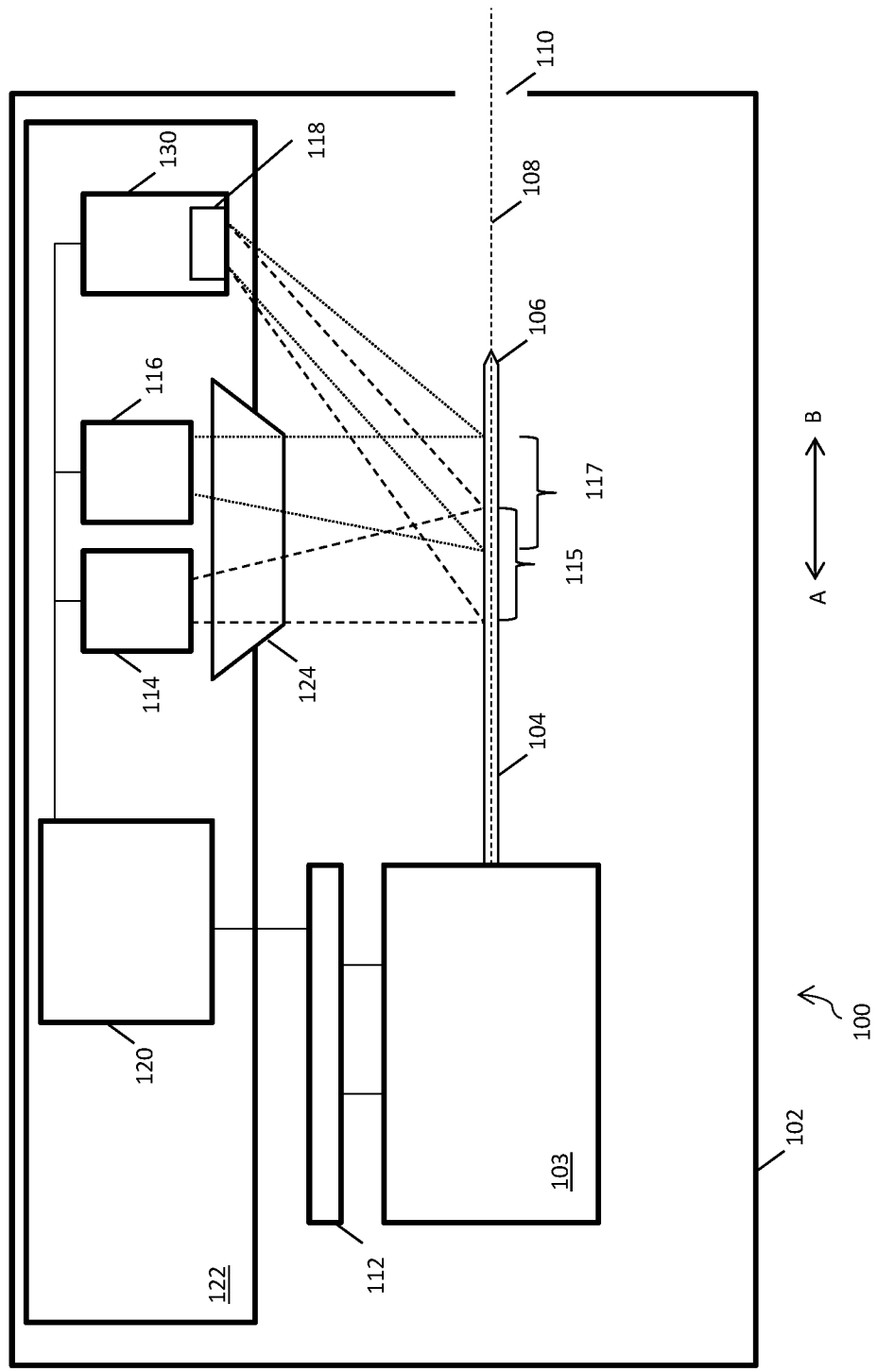
FIG. 1 shows a schematic of an injection system.

FIG. 1 shows an autoinjector 100 for detecting the location of a tip 106 of a needle 104 of an autoinjector 100. The autoinjector 100 has a housing 102, which can be opened in order to insert a syringe or other medicament container (such as a cartridge) 103 either having a needle 104 or with which a removable needle 104 can engage. The needle 104 is a hypodermic needle, the tip 106 of which being suitable for piercing a patient's skin. The autoinjector 100 can be used to inject a predetermined dose of a medicament into the patient. Once the medicament has been administered and the needle 104 withdrawn from the patient, the user can open the housing 102 and remove the medicament container 103. Further, when the time comes to inject again, the user can open the housing 102, insert another medicament container, and repeat the process. The autoinjector housing 102 contains an actuator 112 which may be a linear actuator and which is operable to move the needle 104 along a needle path 108. When a needle is placed in the autoinjector, the long axis of the needle lies on the needle path. The housing 102 also comprises an aperture 110, through which the needle 104 can project beyond the housing 102 in order to inject the patient. Operation of the actuator 112 causes the needle 104 to move in direction A-B, for example so as to cause the needle 104 to move towards the aperture 110 in direction B and eventually project therebeyond or alternatively so as to cause the needle 104 to move in the opposite direction, in direction A, and retract back within the housing 102.

The autoinjector 100 also has a first light emitting diode (LED) 114, a second LED 116, and a photodiode detector 118. The LEDs and photodiode detector 118 are positioned on a printed circuit board (PCB) 122, and are electronically coupled to a processor 120. The processor 120, when acting to determine the location of the needle tip 106 in accordance with the below-described method, may be called a location determiner. The actuator 112 is also electronically coupled to the processor 120/location determiner. The actuator 120 produces a signal based on the position of a moving actuator component, and sends this signal to the processor 120.

The actuator 112 is arranged to move the needle 104 along a trajectory or path 108. In an extension phase, the actuator 112 drives the needle 104 along the path 108 towards and through the aperture 110 until at least a portion of the needle 104, including the needle tip 106, projects externally beyond the aperture 110. During this phase, the actuator 112 advances the needle 104 at a substantially constant speed along the path 108. For example, the actuator 112 may drive the needle 104 at 6.6, 10, or 20 mms$^{-1}$. Once the needle tip 106 projects beyond the interior of the housing 102, it can be used to pierce the skin of a patient. The actuator 112 can continue to advance the needle 104 along the path 108 until a required injection depth is reached. The actuator 112 is also arranged to press a plunger of the syringe or cartridge, in order to administer the medicament via the needle 104 into the patient's body.

During a retraction phase, the actuator 112 can move the needle 104 along the path 108 in an opposite direction to the direction used during the extension phase, in order to withdraw the needle 104 from the patient and retract it back inside the housing 102.

The LEDs 114, 116 are positioned adjacent to each other on a surface of the PCB 122. The first LED 114 is arranged to shine light on a first portion 115 of the needle path 108. Light from the first LED 114 is shown in FIG. 1 using dashed lines. The second LED 116 is arranged to shine light on a second portion 117 of the needle path 108. Light from the second LED 116 is shown in FIG. 1 using dotted lines. For a needle 104 that has been installed in the autoinjector 100, the path 108 generally extends substantially along the long axis of the needle 104 although other paths may be employed. Starting from a fully retracted position, as the needle 104 is moved in direction A along the path 108 during the extension phase the needle tip 106 encounters the first portion 115 of the path 108, then the second portion 117 of the path 108, and then the aperture 110. In FIG. 1 the needle tip 106 has advanced through the first portion 115 and second portion 117 of the path 108, but has not yet reached the aperture 110.

The autoinjector 100 also comprises a signal producer 130, which comprises the photodiode detector 118. The photodiode detector 118 is positioned on a surface of the PCB 122. The photodiode detector 118 may be a wide acceptance angle detector. The photodiode detector 118 can receive and detect light which has been both emitted by the first LED 114 and reflected by the needle 104. The photodiode detector 118 can also receive and detect light which has been both emitted by the second LED 116 and reflected by the needle 104. The photodiode detector 118 may be arranged near the first and second LEDs 114, 116 on the PCB 122 in order to receive light reflected by the needle 104 at substantially 180° to its angle of incidence with the needle 104. This arrangement can reduce the amount of ambient light received by the photodiode detector 118.

The light from each LED is baffled and guided using a lens 124. The lens 124 is a custom biconic or prism part mounted above the PCB 122. The lens 124 is positioned over the first LED 114 and the second LED 116, allowing a narrow plane of light to be created comprising light planes originating from each LED. The two planes of light have intensity maximums at slightly separated spatial locations across the direction of needle travel. The lens 124 allows light emitted by the first LED 114 and the second LED 116 to be shaped and collimated.

Figure 2:
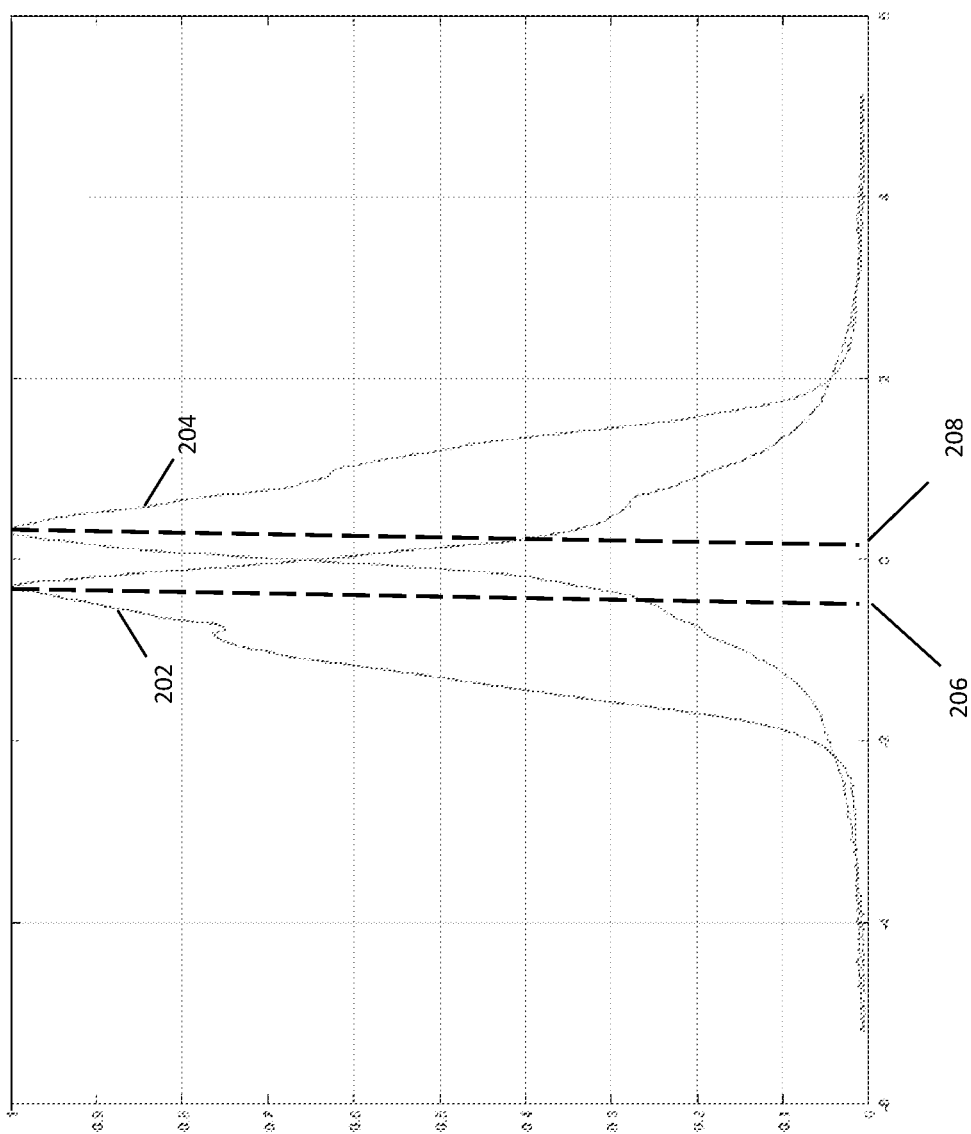
FIG. 2 shows a graph of light profiles at a needle plane.

FIG. 2 shows an experimentally obtained graph of the light intensity profiles from each LED at the needle path 108. The y-axis shows the normalised intensity of light received by a detector positioned at various points along the needle path 108. Such a detector is not generally part of the autoinjector 100, and was placed at various points along the needle path 108 in order to plot the light intensity profiles from each beam at the path 108. The x-axis shows the position along the path 108 of the detector, measured in mm, with the origin, at zero mm, being representative of a position along the path 108 between a first beam of light emitted by the first LED 114 and a second beam of light emitted by the second LED 116.

The trace on the left, 202, represents the intensity of light emitted by the first LED 114 and detected by a light detector at certain positions along the needle path 108. The trace on the right, 204, represents the intensity of light emitted by the second LED 116 and detected by a light detector at certain positions along the needle path 108. As will be appreciated by the skilled person, the respective beams from the first LED 114 and the second LED 116 are spatially separated.

The trace on the left 202 is associated with a first portion of the path 108, which is illuminated by the first LED 114. The trace on the right 204 is associated with a second portion of the path 108, which is illuminated by the second LED 116. The first and second portions may overlap on the path 108, and may also encompass different regions of the path 108.

The intensity profile of light from the first LED 114 may be at a maximum on a first point 206 of the path. The intensity profile of light from the second LED 116 may be at a maximum at a second point 208 of the path. The first point 204 on the path is at a different position along the path to the second point on the path 208. The illumination profiles of light emitted by the first LED 114 and second LED 116 are respectively centred on the first point 206 and the second point 208 of the path.

The system will now be described in operation, with reference to FIGS. 1 to 3.

Figure 3:
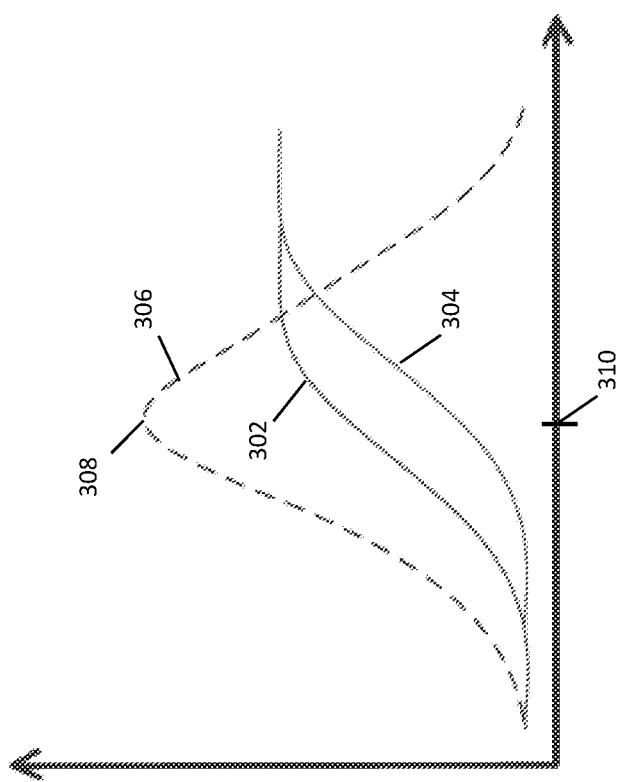
FIG. 3 shows a graph of signals produced by a signal producer as a needle is advanced along a trajectory.

FIG. 3 is a graph which shows the amplitude of a first signal 302 and a second signal 304 produced by the signal producer 130 as the needle 104 is moved along the path 108. The x-axis shows the position of the needle tip 106 on the path 108.

When the needle 104 is fully retracted, a negligible amount of light from either the first or the second light source is incident on the needle 104, the needle tip 106, or the photodiode detector 118. As the actuator 112 moves the needle 104 from a fully retracted position along the path 108 in direction B, the needle 104 is advanced into the first portion 115 of the path 108, and into the light emitted by the first LED 114. As the needle 104 is advanced further along the path 108, light from the first LED 114 is incident on a greater proportion of the needle 104, and therefore more light emitted by the first LED is reflected by the needle 104. The photodiode detector 118, and hence the signal producer 130, receives at least part of this reflected light, and produces a first signal 302. The first signal 302 is representative of the amount of light received by the signal producer 130 which has been both emitted by the first LED 114 and reflected by the needle 104. The amplitude of the first signal 302 increases as more of the surface of the needle 104 is advanced into the first portion 115 of the path 108, i.e. as more light from the first LED 114 is incident on the reflective surfaces of the needle 104 and needle tip 106.

As the actuator 112 continues to advance the needle 104 in direction B, the needle 104 is advanced into the second portion 117 of the path 108, and into the light emitted by the second LED 116. As the needle 104 is advanced further along the path 108, light from the second LED 116 is incident on a greater proportion of the needle 104, and therefore more light emitted by the second LED is reflected by the needle 104. The signal producer 130 receives at least part of this reflected light, and produces a second signal 304. The second signal 304 is representative of the amount of light received by the signal producer 130 which has been both emitted by the second LED 116 and reflected by the needle 104. The amplitude of the second signal 304 increases as more of the surface of the needle 104 is advanced into the second portion 117 of the path 108, i.e. as more light from the second LED 116 is incident on the reflective surfaces of the needle 104 and needle tip 106.

As can be appreciated from FIG. 3, the amplitude of the first signal 302 increases as the needle 104 is extended along the path 108. The increase in amplitude of the first signal 302 as the needle 104 is advanced along the path 108 in direction B is associated with an increase in the proportion of the first portion 115 of the path 108 which is occupied by the needle 104. As the needle 104 occupies an increasing proportion of the first portion up until approximately half of the first portion 115 of the path 108 is occupied by the needle 104, the amplitude of the first signal 302 increases quickly. As over half of the first portion is occupied by the needle 104, the amplitude of the first signal 302 increases more slowly. As the needle 104 comes to occupy a majority, or all, of the first portion 115 of the path 108, the amplitude of the first signal 302 stops increasing.

Similarly, the amplitude of the second signal 304 increases as the needle 104 is further extended along the path 108. The second portion 117 of the path 108 is illuminated by the second LED 116, and the increase in amplitude of the second signal 304 as the needle 104 is advanced along the path 108 toward the aperture is associated with an increase in the proportion of the second portion 117 which is occupied by the needle 104. As the needle 104 occupies an increasing proportion of the second portion up until approximately half of the second portion 117 of the path 108 is occupied by the needle 104, the amplitude of the second signal 304 increases quickly. As over half of the second portion 117 is occupied by the needle 104, the amplitude of the second signal 304 increases more slowly. As the needle 104 comes to occupy a majority, or all, of the second portion 117 of the path 108, the amplitude of the second signal 304 stops increasing.

As well as depicting the first signal 302 and the second signal 304, the graph shown in FIG. 3 also depicts the differentiated ratio 306 of the first and second signal 304 as the needle 104 is moved along the path 108. The differentiated ratio 306 may also be called a differential ratiometric signal. The differentiated ratio 306 is calculated by differentiating the ratio of the first signal 302 and the second signal 304. The differential of the ratio of the first signal 302 and the second signal 304 reaches a peak 308 when the difference in amplitude between the first and the second signal 304 is at a maximum.

The position 310 of the needle 104 when the differentiated ratio 306 is at a maximum 308 is determined by the spatial separation of the light emitted by the first LED 114 onto the path 108 and the light emitted by the second LED 116 onto the path 108. The position 310 of the needle when the differentiated ratio 306 is at a maximum lies between points 206 and 208 of the path. In some examples, the position 310 of the needle when the differentiated ratio 306 is at a maximum 308 may be the point at which the needle tip 106 has advanced far enough along the path 108 to reflect light emitted by the first LED 114, but has not advanced far enough along the path 108 to reflect light emitted by the second LED 116.

The position 310 of the needle associated with the maximum 308 of the differentiated ratio 306 may be a predetermined position along the path 108. For example, point 310 may be halfway between the first portion 115 of the path and the second portion 117 of the path 108, and/or halfway between the first point on the path 206 and the second point 208 on the path 108. The predetermined position may thus be predetermined by design and placement of the lens 124 and the first and second LEDS 114, 116. Manufacturing tolerances may be compensated for by calibration.

The first signal 302 and second signal 304 and the differentiated ratiometric signal 306 are functions of x, the position of the needle 104 on the needle path 108. Accordingly, those signals are also a function of the amount of extension of the actuator 112. The amount of extension of the actuator may be associated with the position of a moving component of the actuator 112. The location of the needle tip along the path is also therefore a function of the extension of the actuator. The actuator may have several well-defined positions, such as the position of, or the degree of rotation of, a lead screw within the actuator. The actuator produces a signal based on the amount of extension of an actuating component, and sends this signal to the processor. In some examples, the system notes the actuator signal when the differentiated ratiometric signal is at a maximum. The system thereby allows the position of the needle tip to be determined at any point in time subsequent to the initial determination of needle tip position by reference to the signal produced by the actuator, which is representative of the extension of the actuator.

The needle tip 106 can therefore be located by finding the peak 308 of the differential ratiometric signal 306 as the needle 104 moves along the path 108 and passes through light emitted by the first LED 114 and the second LED 116. When the peak 308 of the differentiated ratio 306 metric signal is located, the processor 120 may be operable to record the extension of the actuator 112. The extension of the actuator 118 is thus noted when the differential ratiometric signal 306 is at a maximum 308. The extension of the actuator 118 when the differential ratiometric signal 306 is at a maximum 308 may correspond with the needle tip 106 being at a predetermined position 310. Given knowledge of the extension of the actuator 112 when the differentiated ratiometric signal is at maximum, the position of the needle 104 at any subsequent time can be calculated by the processor 120, given knowledge of the actuator 112 extension at the subsequent time.

Determination of the location of the tip 106 of the needle 104 allows the depth of any subsequent injection to be calculated. A fixed distance between the position 310 and the aperture 110 may also be factored into the calculation of injection depth.

Ratiometric measurement is beneficial as it is insensitive to variations in needle size, and therefore signal amplitude. During signal acquisition it is possible to compare the ratio of the two curves using the following formula:

$$R(x)=S_1(x)/S_2(x)$$

where x represents the position of the needle 104 along the path 108, and $S_1(x)$ and $S_2(x)$ correspond to the first signal 302 and second signal 306 respectively, and R(x) is the ratio of $S_1(x)$ and $S_2(x)$. The slope of R, i.e. the differentiated ratio 306, is given by:

$$\frac{dR(x)}{dx}$$

Time divisional multiplexing (TDM) can be used to encode the first and second signals 302, 304 so as to enable discrimination therebetween—for example in cases where the light produced by the LEDs 114, 116 cannot be optically differentiated.

Of course, it will be appreciated that it is also possible to differentiate each of $S_1(x)$ and $S_2(x)$ first, and then take the ratio of the differentiated signals. This approach will also result in a signal and curve similar to 306 and 308 shown in FIG. 3. If the actuator 112 moves at a constant or substantially constant speed, it will be appreciated that it is also possible to differentiate with respect to time, rather than x.

Figure 4:
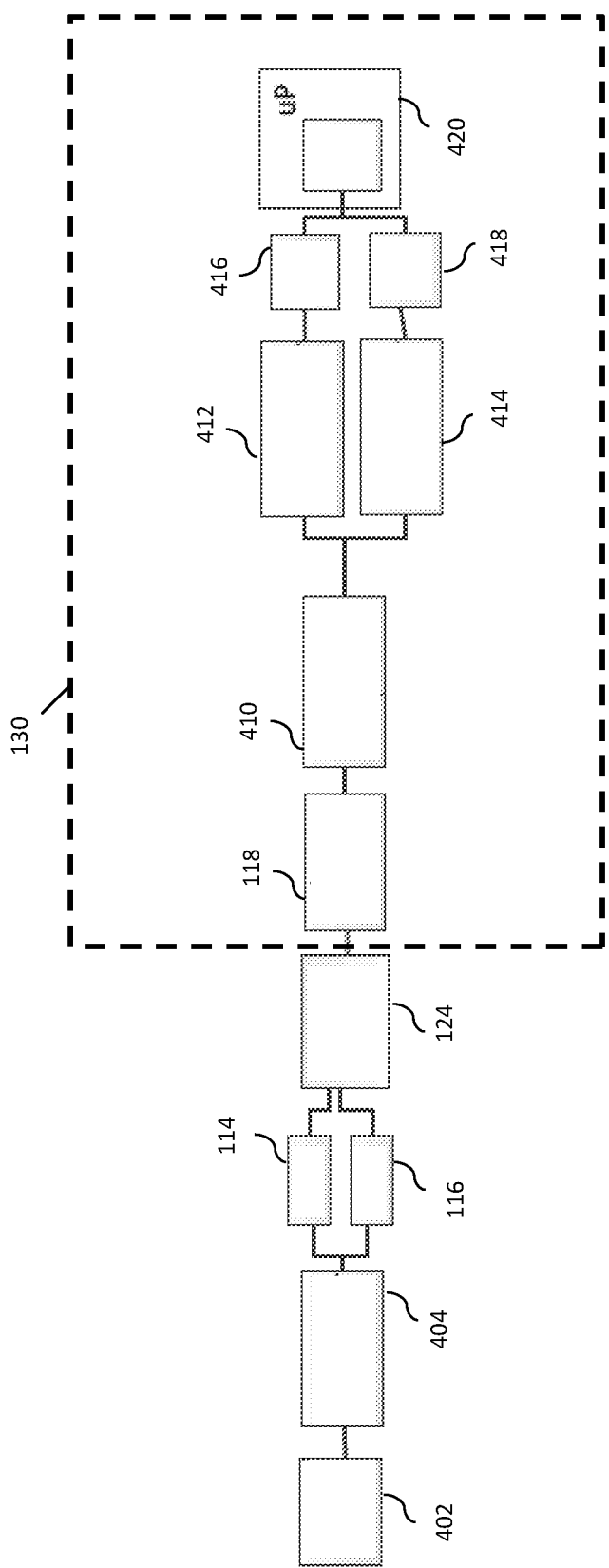
FIG. 4 shows a signal processing chain.

FIG. 4 shows a signal processing chain which can be used to perform a time division multiplexing process. The approach is based on a trans-impedance amplifier technique together with LED modulation and subsequent demodulation on the detection side. The signal processing chain 400 comprises a signal producer 130. The operation of the signal processing chain 400 will now be described.

An LED driver 402 is arranged to supply power to each of the first and second LEDs 114, 116. A modulator 404 is arranged to modulate the power supplied by the LED driver 402 to each LED 114, 116. The LED driver 402 and modulator 404 are arranged to switch each of the first and second LEDS 114, 116 on and off respectively in order to produce pulses of light.

Pulses of light emitted by the first LED 114 are conveyed, via the lens 124 and reflection by the needle 104, to the signal producer 130. The signal producer 130 comprises a photodiode detector 118, an amplifier 410, a first demodulator 412 arranged to process a first unprocessed signal and a second demodulator 414 arranged to process a second unprocessed signal. A low pass filter 416 is arranged to receive a first demodulated signal from the first demodulator 412, and a second low-pass filter 418 is arranged to receive a second demodulated signal from the second demodulator 414. Both the first low pass filter 416 and the second low pass filter 418 are arranged to pass respective demodulated, filtered signals to an analogue to digital converter 420. The analogue to digital converter 420 then passes the digital signal produced by the signal producer to the processor.

The modulation process is beneficial as it helps to reduce noise in the signal caused by ambient light. Ambient light may enter the housing 102 of the autoinjector 100, for example through small gaps in the housing 102 or through the aperture 110, and may be incident on the photodiode detector 118. By modulating the light emitted by the first and the second LED 114, 116, and demodulating the unprocessed signals received by the signal producer, any noise in the unprocessed signal received by the signal producer 130 can be removed.

Figure 5:
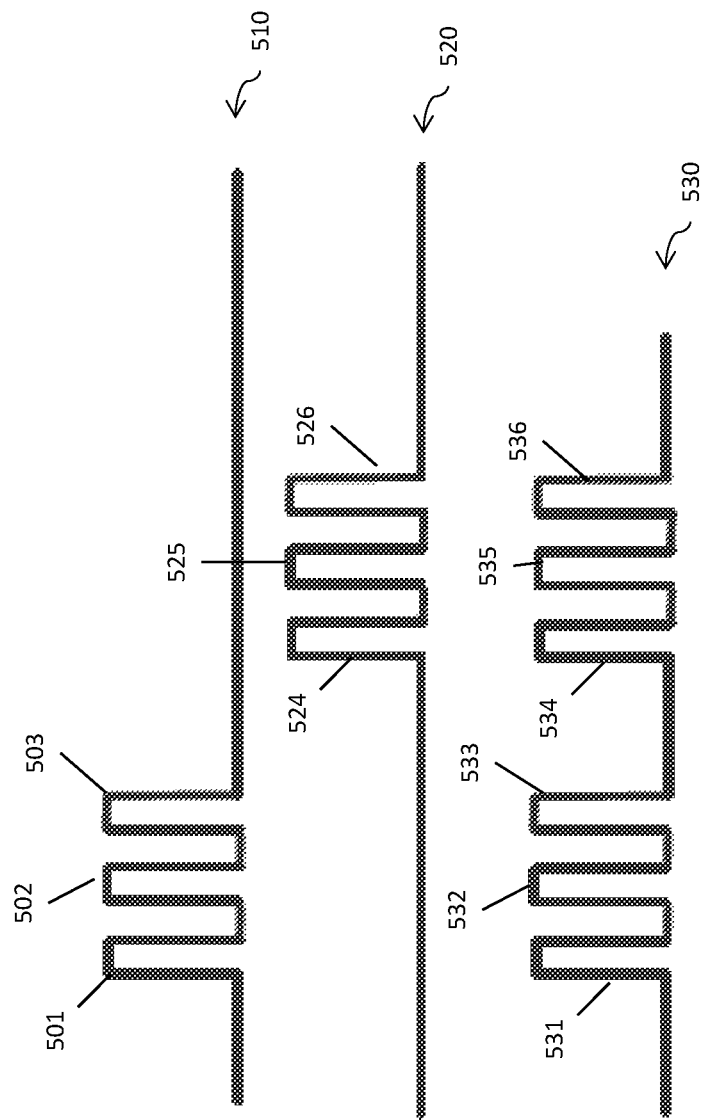
FIG. 5 shows a schematic representation of signals produced by light sources and by the signal producer.

FIG. 5 shows a schematic representation of pulses of light 501, 502, 503 produced by the first LED 114, pulses of light 524, 525, 526 produced by the second LED 116, and unprocessed signals 531-536, produced by signal producer 130. The top line 510 of FIG. 5 shows an example in which the first LED 114 is driven on and off three times to give three pulses of light, 501, 502, 503. If the needle 104 is occupying a position such that the three pulses can be reflected by the needle 104, the three pulses are detected by the photodiode detector 118. The bottom line 530 of FIG. 5 shows the unprocessed signals produced by the photodiode detector 118 as the three light pulses 531, 532, 533 emitted by the first LED 114 are detected. The middle line 520 of FIG. 5 shows a similar process being repeated with the second LED 116 at a different time, with three pulses of light being produced 524, 525, 526, and the bottom line 530 showing the unprocessed signals 534, 535, 536 produced by the photodiode detector 118 as the three light pulses 524 525, 526 emitted by the second LED 114 are detected.

The unprocessed signals produced by the photodiode detector 118 are passed to the amplifier 410 and then to the pair of demodulators 412, 414 for respective separate demodulation of the first and second unprocessed signals so as to produce the respective first and second signals 202, 204. The first and second unprocessed signals are each be passed through a respective low pass filter 416, 418, prior to being conveyed to an analogue to digital signal converter 420.

It will be appreciated that the above-described Time Division Multiplexing (TDM) method is an example of how time division multiplexing could be used to produce two independent signals based on respective light emitted by the first LED 114 and the second LED 116, and that other suitable TDM techniques may equally be employed.

Figure 6:
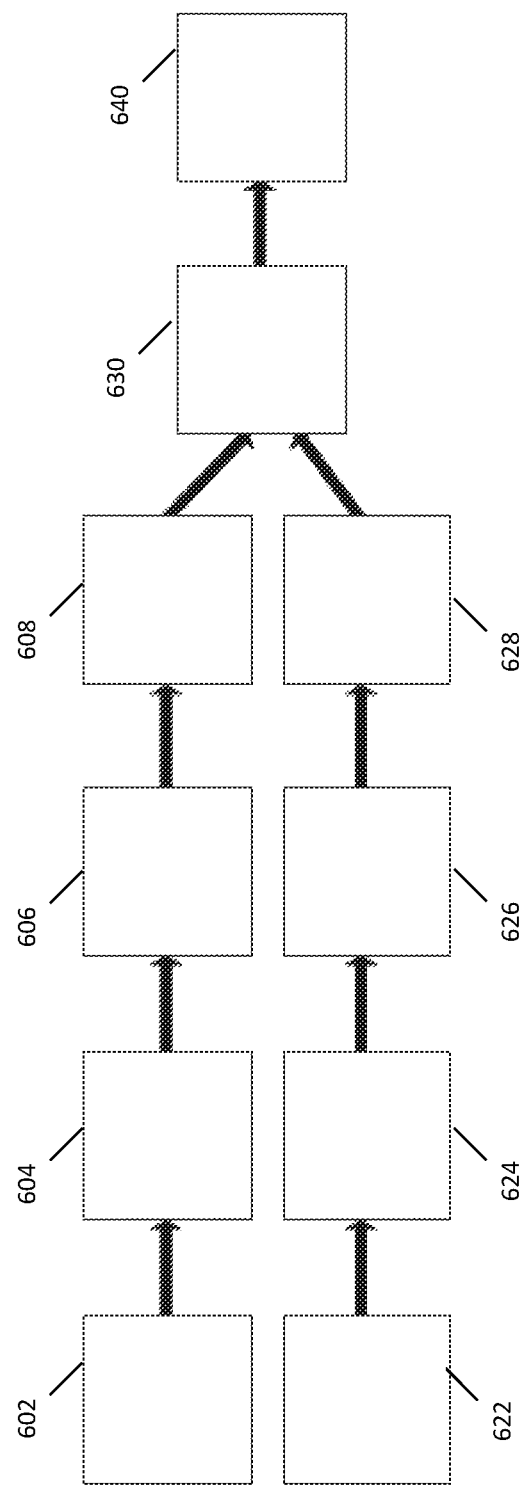
FIG. 6 shows a signal processing flowchart.

FIG. 6 shows an example of a signal processing workflow. Initially, the light detected by the photodiode detector 118 undergoes a time division multiplexing process to produce a first unprocessed signal 602 associated with light emitted by the first LED 114 and a second unprocessed signal 622 associated with light emitted by the second LED 116. A low-pass filter 604, 624 is applied to each of the respective unprocessed signals 602, 604 to remove any high frequency noise components. A high-pass filter 606, 626 is then applied to the low-pass filtered signals. It is possible to obtain the function of a differentiator using a simple high-pass filter, as is known, and therefore the high pass filter can be used to differentiate the respective low-pass filtered signals. A signal threshold 608, 628 is applied to each high-pass filtered signal to remove any significant noise components at low amplitudes, and the ratio of the resulting signals is taken at 630. Finally, the differentiated ratiometric signal is output at 640.

Figure 7:
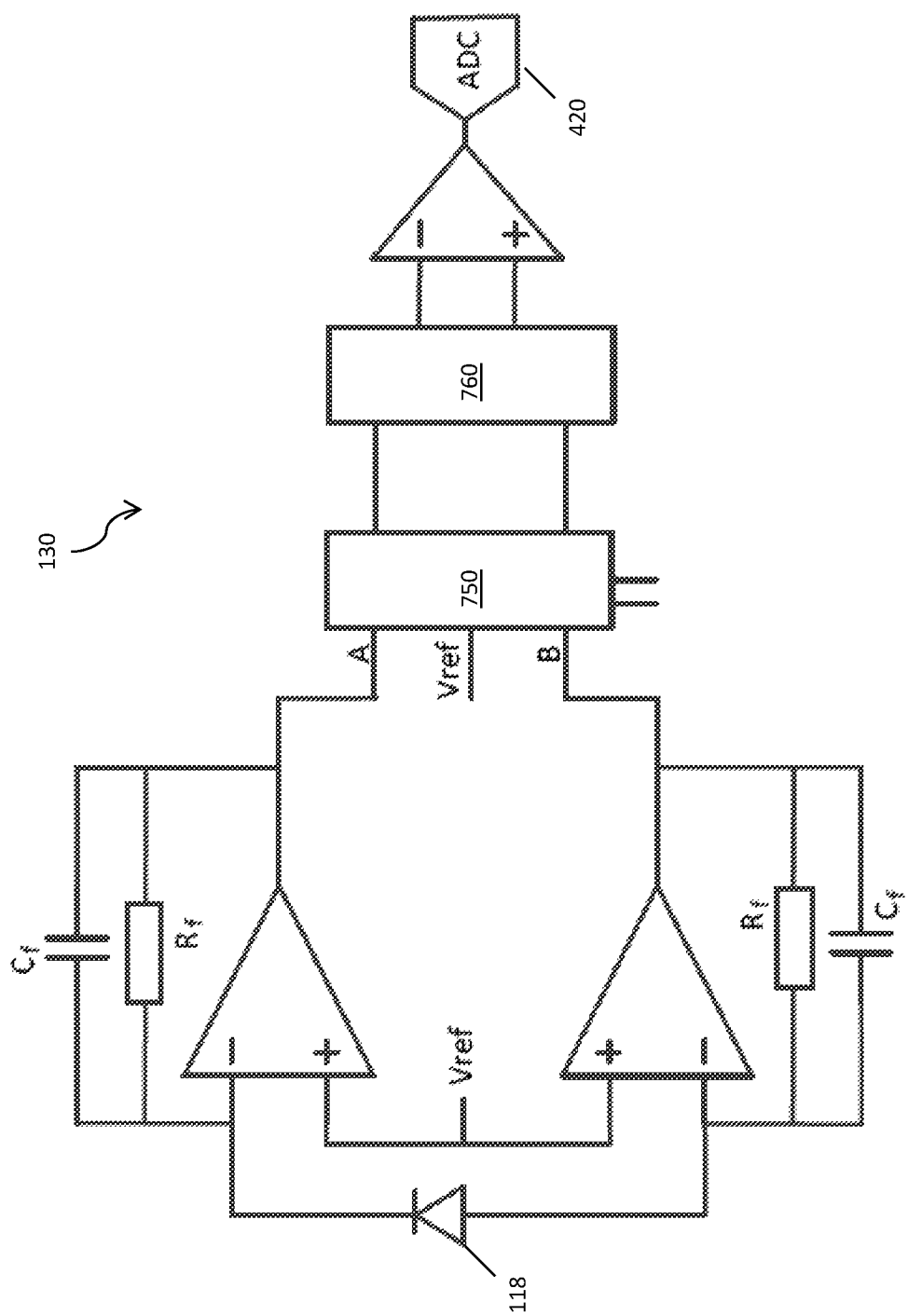
FIG. 7 shows an example of a circuit design for a signal producer.

FIG. 7 shows a schematic diagram of a circuit design for a signal producer 130. The signal producer 130 may be arranged to process optical signals in accordance with the above-described method. The diagram shows a circuit that relies on a transimpedance amplifier followed by a demodulator 750 and a low pass filter 760. The low pass filter 760 may have a cut-off frequency equivalent to the highest bound of the bandwidth of the input signal. The circuit may include a photodiode 118, resistors, amplifiers, a switching network (demodulator) 750, a $3^{rd}$ order low pass filter 760, a differential amplifier, capacitors, digital inputs, and an analogue to digital signal converter 420.

The approaches described herein enable the position of the needle tip to be detected to a high degree of accuracy, such that injections given using the autoinjector can be given to accurate depths.

Each part of an autoinjector for a medicament, and indeed the medicament container itself, is manufactured to a certain specification and to a certain tolerance, using, for example, injection moulding techniques. Putting together multiple parts having tolerances, such as a syringe plunger and multiple actuator results in an inevitable 'tolerance stack'. Autoinjectors also typically allow a user to remove and insert medicament containers such as syringes, meaning that the container may be incorrectly inserted into the housing. The tolerance stack, and the variable placement and orientation of the syringe in the autoinjector, may result in a relatively large error associated with the location of the needle tip at any one moment. This creates a corresponding error in any calculation of injection depth.

The system disclosed herein can be used to determine an accurate position of the needle tip, which mitigates error associated with the 'tolerance stack' and in turn allowing more accurate injection depth to be calculated.

There are other advantages associated with the present system, for example positioning the photodiode detector adjacent to, or at least near to, the first LED and/or the second LED means that the photodiode detector is positioned to detect signals which have been reflected by the needle through substantially 180°. This reduces the detection of ambient light from light ingress into the autoinjector.

It will be appreciated that although a signal producer comprising a photodiode detector has been described, any other suitable photo detector, light detector or light sensor could be used, for example a charge-coupled device (CCD), a photo resistor, a phototransistor, or a semiconductor detector.

It should also be appreciated that, although a system comprising LEDs has been described, any other suitable light source other than an LED could be employed, such as a laser.

In some examples, the aperture may comprise a shutter, which is moveable to block and unblock the aperture. The shutter may be operated by the processor. The shutter may be operable to unblock the aperture just before the needle is extended through the aperture, and block the aperture again when the needle is retracted back within the housing. Information from the system, for example regarding the location of the needle tip, may feed into the calculation of when the shutter should open. Blocking the aperture reduces the amount of ambient light which may be incident on the signal producer, and therefore may reduce the error associated with locating the needle tip position, it may also help keep the interior of the autoinjector clean. As another possibility, the aperture may be mechanically coupled to the medicament container and/or the needle so that advancement of the needle along the needle path towards the aperture causes the shutter to open and subsequent retraction of the needle from the aperture causes the shutter to close.

In another example, the first LED and the second LED may be replaced by a single LED, or another single light source, and filters may be used to create two 'effective' light sources. For example, a single LED may shine on two filters that are controllable to change between opaque and transparent states. With light from the single light source incident on the two filters, the filters may be driven in order to produce pulses of light, for example in accordance with FIG. 5, to simulate two light sources.

In another example, the first LED and the second LED may shine light having different frequencies. It would then be possible to separate the first and the second signals into respective channels using a frequency division multiplexing by way of frequency specific photodetectors.

Figure 8:
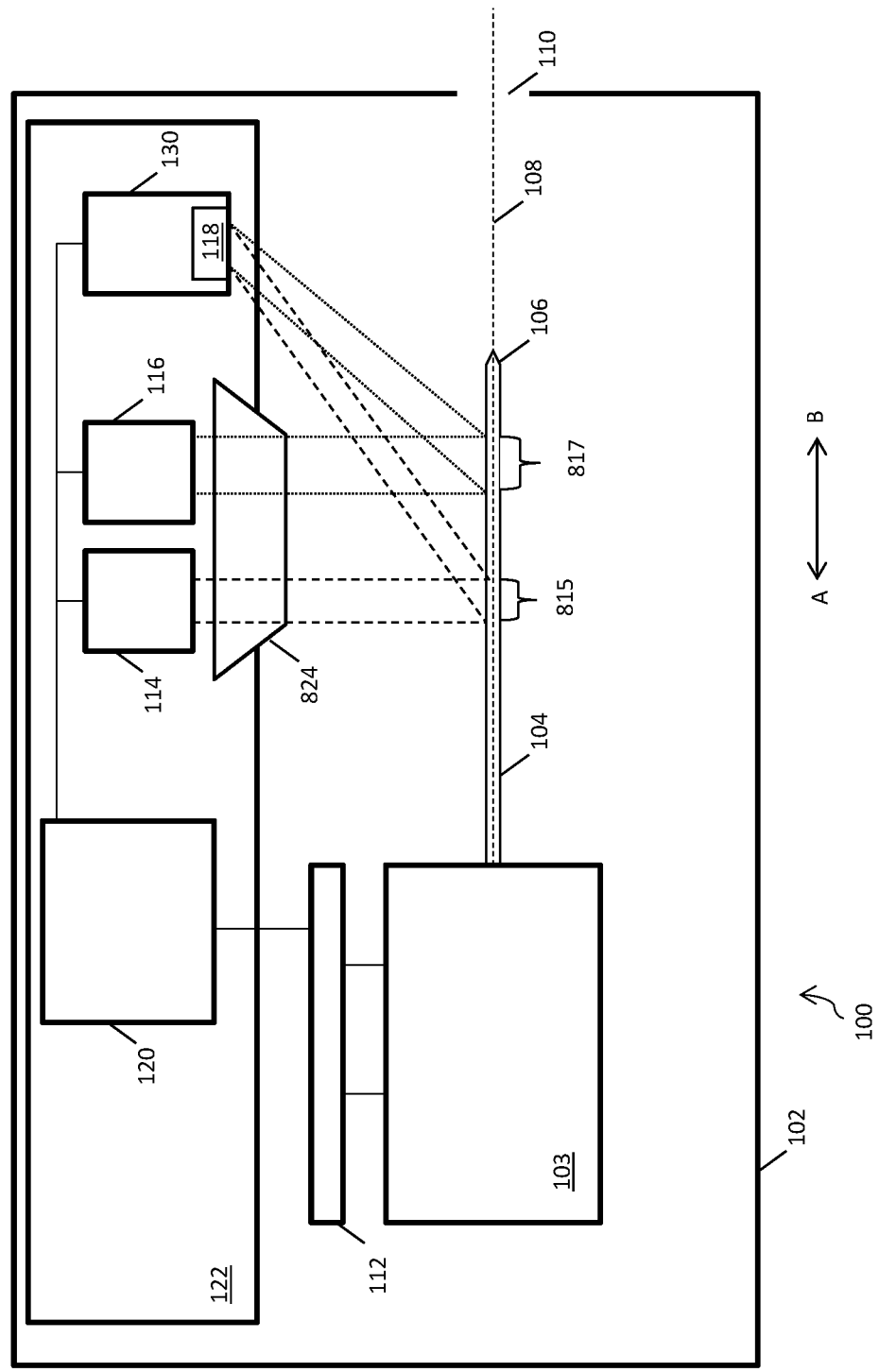
FIG. 8 shows a schematic of another injection system.

Turning to FIG. 8, in another example, rather than have a first portion 115 of the needle path 108 illuminated by light from the first LED 114 with an intensity maximum at a first point 206 along the path 108, and a second portion 117 of the needle path 108 illuminated by light from the second LED 116 with an intensity maximum at a second point 208 along the path 108, optical components such as a lens 824 may be employed in order to produce two narrow beams or planes of light. Alternatively, the LEDs may be replaced with respective lasers. In this examples, the first portion 815 of the path 108 which is illuminated by light from the first LED 114, does not overlap with the second portion 817 of the path which is illuminated by the second LED 116. The resultant light shining on the path 108 from both the first and the second beams is coplanar and collimated. The method of detecting the needle position in this example is functionally equivalent to the method described above, with the system being able to detect when the needle tip 106 is substantially halfway between the first portion 815 and the second portion 817 of the path 108.

Figure 9:
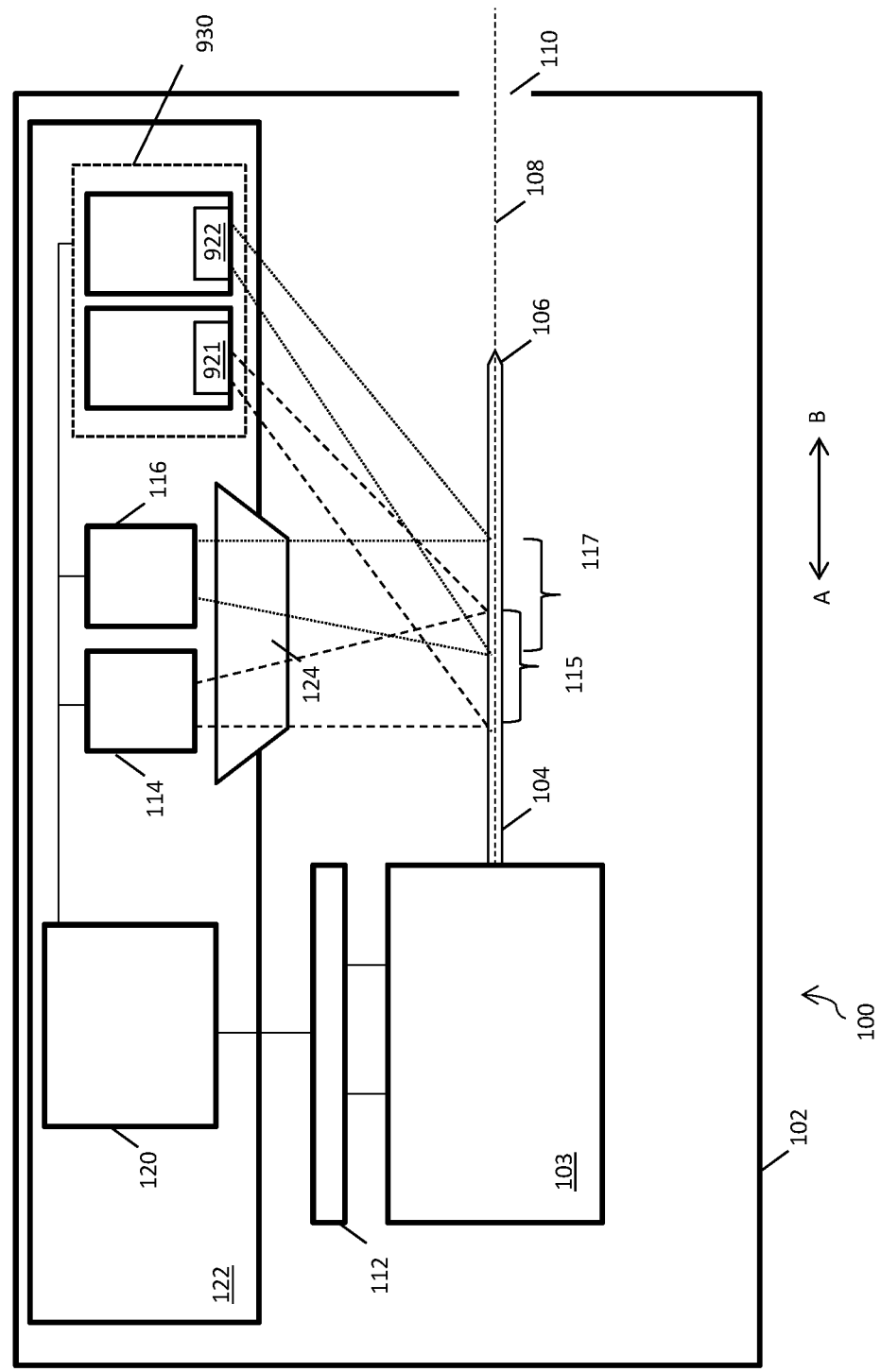
FIG. 9 shows a schematic of another injection system.

Turning to FIG. 9, in another example the signal producer 920 may comprise both a first photodiode detector 921 and a second photodiode detector 922, each positioned to receive respective light emitted by the first LED 114 and the second LED 116. This approach may simplify the signal processing steps detailed above, as would be appreciated by the skilled person.

Whilst the system has been described having one lens arranged above the PCB 122 in order to focus light emitted from both the first LED 114 and the second LED 116, the skilled person will also appreciate that it is possible to use two respective lenses in the system; one for each LED.

In some variants of the system, the sensor may not perform equally for all orientations of the needle. For example, where the needle tip has bevelled surfaces, anomalous reflections are produced when the bevelled surfaces of the needle tip reflect light toward the photodiode detector. One way of addressing this problem is to use two light sources and two photodiode detectors and position the first light source and its associated photodiode detector orthogonally with respect to the second light source and its associated photodiode detector. In this way, anomalous signals due to specific needle orientations at the first photodiode detector may be accounted for by reference to signals received by the second photodiode detector.

In one example, a third LED and a fourth LED are located in the autoinjector housing. Those LEDs are positioned to shine light in a direction toward the path of the needle, but in a direction different to, for example orthogonal to, the direction of light emitted by the first LED and the second LED. A second photodiode detector may be positioned to detect light which has been both emitted by one of the third and fourth LEDs, and reflected by the needle. In this example, the third LED, fourth LED, and second photodiode detector operate with the processor and the actuator in much the same manner as described above in relation to the first LED, second LED and first photodiode detector. Arranging the third and fourth LEDs to shine light in a direction orthogonal to the light emitted by the first and second LEDs reduces the amount of light 'crosstalk' between systems. The use of signals in two independent planes means the non-bevelled surface of the needle will always be facing at least one of the planes of detection, resulting in an appropriate signal being acquired in at least one of the planes.

Figure 10:
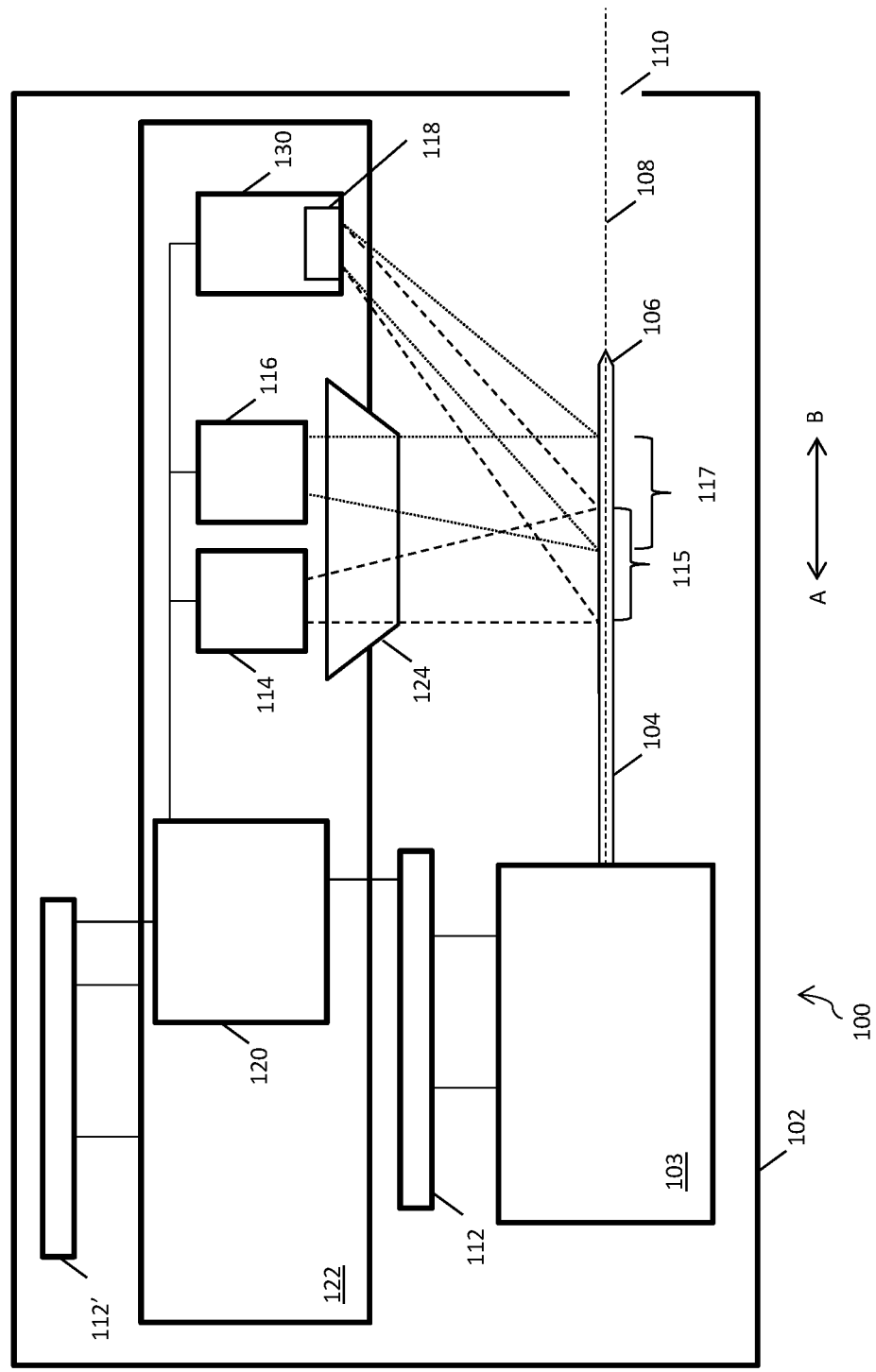
FIG. 10 shows a schematic view of another injection system.

Turning to FIG. 10, in another example, the system optics, such as the first LED 114, second LED 116 and the photodiode detector 118, are moved relative to the needle. This movement may be referred to as scanning. The first LED 11, second LED 116, and photodiode detector 118 are positioned on the printed circuit board (PCB) 122, and are electronically coupled to a processor 120. Optics actuator 112' is arranged to move the PCB 122 within the housing 102 of the autoinjector 100 in a direction defined by the arrow A-B on FIG. 10. The lens 124 may also be coupled to the moveable PCB.

In this example, rather than the needle being moved relative to light emitted by light sources, such as stationary LEDs, the light sources, in this case LEDs, are moved relative to the needle by the actuator 112'. The needle may itself also be moved by actuator 112 in the direction A-B. Relative movement of the system optics and the needle 104 can therefore be effected by one or both of actuators 112, 112'. Actuators 112 and 112' operate together to form an actuating system.

The system of FIG. 10 operates in a similar manner to the system described above. As the first LED is moved relative to the needle 106, the light from the first LED 114 may become incident on a greater proportion of the needle 104. When this occurs, more light emitted by the first LED is reflected by the needle 104. The amount of light received by the photodiode detector 118 which has been both emitted by the first LED 114 and reflected by the needle 104 increases, and therefore the amplitude of the first signal 302 produced by the signal producer 130 increases. Similarly, if a greater proportion of light emitted by the second LED 116 is incident on the needle 104, the amount of light received by the photodiode detector 118 which has been both emitted by the second LED 114 and reflected by the needle 104 increases. Therefore, the amplitude of the second signal 306 produced by the signal producer increases.

The system can determine the position of the needle tip 106 based on a relationship between the first signal 302 and the second signal 304, as described above. A signal from the actuating system may also be taken into account, so that the position of the needle tip at all positions of the actuation system can be determined.

It will be appreciated that it is relative movement of the needle and the light produced by the light sources which allows the system to detect the position of the needle tip in this example, and many actuator configurations are possible.

Figure 11:
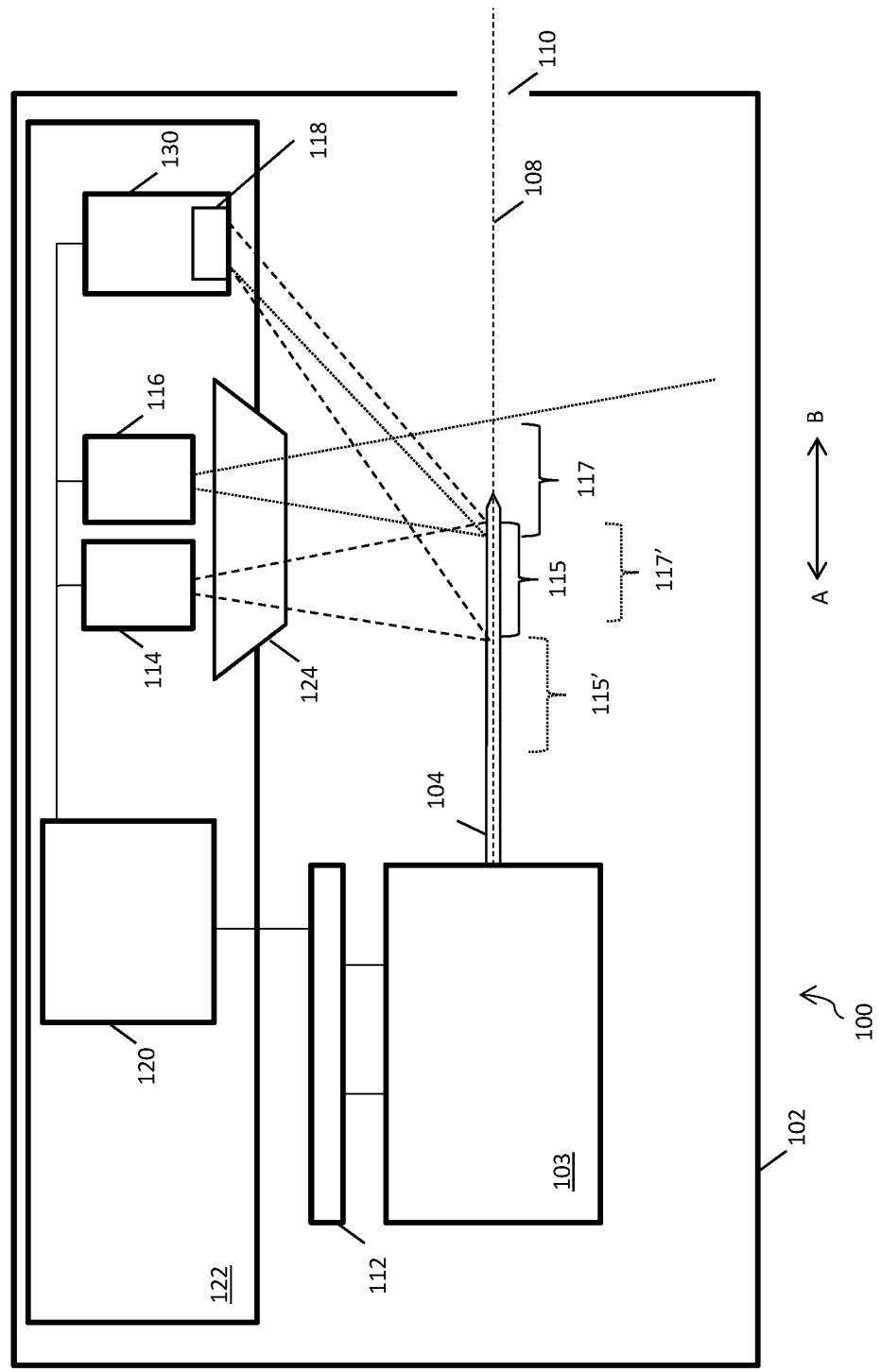
FIG. 11 shows yet another schematic injection system.

Turning to FIG. 11, in another example, an actuating system may scan the light from both the light sources (in this case the first LED 114 and the second LED 116) across the needle. The actuating system may accomplish this by rotating the LEDs so as to change the incident angle of light on the needle and/or by selectively altering one or more properties of the lens 124 such as the transparency, refractive index and/or the distribution of such properties within the lens. As shown by way of example in FIG. 11, the scanning process causes light from the first LED 114 to shine on a portion 115 of the needle path 108. In FIG. 11, the portion of the path 115 is occupied by the needle 104. The scanning process also causes light from the second LED 116 to shine on a second portion of the needle path, 117. In FIG. 11, portion 117 of the path is partly occupied by the needle 104.

The actuating system operates to change the direction in which light is emitted by the first and second LED 114, 116 relative to the needle 104. In FIG. 11, by operation of the actuating system, light from the first LED 114 becomes incident on another portion 115' of the path. Portion 115' of the path is different to portion 115 of the path. In this way, the region of the needle path which is illuminated by the first LED 114 is changed. Similarly, the actuating system operates to change the portion of the path which is illuminated by the second LED 116. In FIG. 11, by operation of the actuating system, light from the second LED 116 becomes incident on another portion 117' of the path. Portion 117' of the path is different to portion 117 of the path.

The system in this example operates in much the same manner as described above, as would be understood by the skilled person. As light from the first LED 114 is scanned along the needle path, different amounts of light will be collected by the photodiode detector according to how much light is reflected by the needle 104. Similarly, as light from the second LED 116 is scanned along the needle path, different amounts of light will be collected by the photodiode detector according to how much light is reflected by the needle 104. The amount of light reflected by the needle is a function of the proportion of the illuminated portion of the path which is taken up by the needle 104.

As in other examples, as light from the first LED 114 is scanned along the path 108 and becomes incident on a greater proportion of the needle 104, more light emitted by the first LED 114 is reflected by the needle 104. The amount of light received by the photodiode detector 118 which has been both emitted by the first LED 114 and reflected by the needle 104 increases, and therefore the amplitude of the first signal 302 produced by the signal producer 130 increases. The second signal is produced in a similar manner as light from the second LED 116 is scanned along the path.

The system can determine the position of the needle tip 106 based on a relationship between the first signal 302 and the second signal 304, as described above. A signal from the actuating system may also be taken into account, so that the position of the needle tip at all positions of the actuation system can be determined.

In the disclosed examples, the word 'path' may refer to a region of space which, when a needle is inserted into the autoinjector, is at least partially occupied by the needle. The needle tip is positioned on the path when a needle is inserted into the autoinjector. The path may extend from a point in space immediately adjacent to the tip of the needle, and may extend along the hollow centre of the needle.

As another possibility, the needle is not moved along the path continuously, but is instead advanced to and stopped at certain positions along the needle path. In this example, the first signal and the second signal, which are both functions of x, can be collected at certain discrete values of x which correspond with positions at which the needle is stopped. When the maximum of the differentiated ratio signal is determined, the extension position of the actuator corresponding to the location of the differential ratiometric signal peak can also be determined in a functionally equivalent manner to the manner described above. As has been described above, this determination allows the position of the needle tip to be determined at subsequent times.

Whilst the above description has referred to a differentiated ratio relationship between the first signal and the second signal being used to determine the position of the needle, it will be appreciated that other relationships between the signals may be used. For example, a differentiated difference curve would give a peak when the needle tip was positioned substantially halfway between the first and the second portions of the path. Other relationships can be employed, such as a simple ratio or a simple difference between the first signal and the second signal.

Once the peak of the differentiated ratiometric signal has been located, the determination of subsequent needle tip location can occur in a number of ways. For example, when the needle reaches the position at which the differentiated ratiometric signal is a maximum, the processor may be operable to produce a timestamp. Given knowledge of the speed of the needle as it advances along the path, and the synchronisation between the needle drive mechanism/actuator and the time at which the needle tip position is at the point when the peak of the differentiated ratiometric signal has been reached, the position of the needle at subsequent times can be calculated by the processor. Accordingly, the depth to which the needle tip has been inserted into a patient's skin can be determined.

As will be appreciated by the skilled person, the processor could be replaced by any suitable control means, for example an Application-Specific Integrated Circuit (ASIC) may be employed.

Disclosed herein is a system for detecting a location of a tip of a needle, the system comprising a first light source and a second light source. A light detector is arranged to receive light reflected by the needle. The light detector is also arranged to produce a first signal when reflected light emitted by the first light source is detected, and produce a second signal when reflected light emitted by the second light source is detected. The location of the tip of the needle can be determined based on a relationship between the first and second signal.

There is described herein a system that determines the location of a tip of a hypodermic needle by moving a needle along a path, shining light from two sources onto respective portions of the path, and analysing signals received from the respective light sources that have been reflected by the needle.

The approaches described herein may be embodied on a computer-readable medium, which may be a non-transitory computer-readable medium. The computer-readable medium carrying computer-readable instructions arranged for execution upon a processor so as to make the processor carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

Those skilled in the art will recognize that a wide variety of modifications, alterations, and combinations can be made with respect to the above described examples without departing from the scope of the disclosed concepts, and that such modifications, alterations, and combinations are to be viewed as being within the ambit of the disclosed concepts.

The invention claimed is:

1. A system for determining the location of a tip of a hypodermic needle in a medical device, the system comprising:
   an actuator arranged to move the tip of the needle along a path within the medical device;
   a first light source arranged to shine light onto a first portion of the path;
   a second light source arranged to shine light onto a second portion of the path;
   a signal producer arranged, consequent to the needle being moved along the path, to:
      produce a first signal based on light from the first light source that has been reflected by the needle and received at the signal producer, and
      produce a second signal based on light from the second light source that has been reflected by the needle and received at the signal producer; and
   a location determiner arranged to determine the location of the tip of the needle based on the first and second signals.

2. A system according to claim 1, wherein the location determiner is arranged to determine the location of the tip of the needle based on a relationship between the first and second signals, the relationship being a function of the needle tip position on the path.

3. A system according to claim 2, wherein the location determiner is arranged to determine the location of the tip of the needle based on the position on the path at which the relationship reaches a maximum.

4. A system according to claim 3, wherein the location determiner is arranged to determine the location of the tip of the needle at subsequent positions of the actuator based on an extension position of the actuator corresponding to the position on the path at which the relationship reached a maximum and a subsequent extension position of the actuator.

5. A system according to claim 1, wherein the first and second light sources are arranged so that:
   a first point on the path lies within the first portion of the path, and the intensity of the light from the first light source on the needle path is at a maximum at the first point; and
   a second, different, point on the path lies within the second portion of the path, and the intensity of the light from the second light source on the needle path is at a maximum at the second point.

6. A system for determining the location of a tip of a hypodermic needle in a medical device, the medical device being arranged to move the tip of the needle along a path within the auto-injector system, the system comprising:
   a first light source arranged to illuminate a respective portion of the path;
   a second light source arranged to illuminate a respective portion of the path;
   an actuating system arranged, when the needle is held by the device such that the needle tip lies on the path, to cause:
      light from the first light source to scan along the path, such that the portion of the path that is illuminated by light from the first light source changes; and
      light from the second light source to scan along the path, such that the portion of the path that is illuminated by light from the second light source changes;
   a signal producer arranged to:
      produce a first signal based on light from the first light source that has been reflected by the needle and received at the signal producer, and
      produce a second signal based on light from the second light source that has been reflected by the needle and received at the signal producer; and
   a location determiner arranged to determine the location of the tip of the needle based on the first and second signals.

7. A method for determining the location of a tip of a hypodermic needle in a medical device including an actuator arranged to move the needle, the method comprising:
   using the actuator to move the tip of the needle along a path within the medical device;
   shining light from a first light source onto a first portion on the path;
   shining light from a second light source onto a second portion on the path;
   receiving light at a signal producer and, consequent to the needle being moved along the path:
   producing a first signal based on light from the first light source that has been reflected by the needle and received at the signal producer;
   producing a second signal based on light from the second light source that has been reflected by the needle and received at the signal producer; and
   determining a location of the tip of the needle based on the first and second signals.

8. A method according to claim 7, wherein the location of the tip of the needle is determined based on a relationship between the first and second signals, the relationship being a function of the needle tip position on the path.

9. A method according to claim 7, wherein the location of the tip of the needle is determined based on a relationship between the first and second signals, the relationship being a function of the needle tip position on the path.

10. A method according to claim 8, wherein the location is determined by determining the position on the path at which the relationship reaches a maximum.

11. A method according to claim 10, further comprising determining an extension position of the actuator when the needle is at the position on the path at which the relationship has reached a maximum, and determining a subsequent needle tip position based on the determined extension position and a subsequent extension position of the actuator.

12. A method according to claim 7, wherein:
   a first point on the path lies within the first portion of the path, and wherein the intensity of the light from the first light source on the needle path is at a maximum at the first point; and
   a second, different, point on the path lies within the second portion of the path, and wherein the intensity of the light from the second light source on the needle path is at a maximum at the second point.

13. A method for determining the location of a tip of a hypodermic needle of a handheld medical device, the handheld medical device being arranged to move the tip of the needle along a path within the auto-injector system, the method comprising:
   shining light from a first light source on a respective portion of the path;
   shining light from a second light source on a respective portion of the path;
   when the needle is held by the device such that the needle tip lies on the path:

scanning light from the first light source along the path, such that the portion of the path that is illuminated by light from the first light source changes; and scanning light from the second light source along the path, such that the portion of the path that is illuminated by light from the second light source changes;

producing a first signal based on light from the first light source that has been reflected by the needle and received at the signal producer;

producing a second signal based on light from the second light source that has been reflected by the needle and received at the signal producer; and determining a location of the tip of the needle based on the first and second signals.

14. A non-transitory computer readable medium comprising machine readable instructions arranged, when executed by one or more processors, to cause the one or more processors to carry out the method of claim 7.

* * * * *